US007838639B2

(12) United States Patent
Tschopp et al.

(10) Patent No.: US 7,838,639 B2
(45) Date of Patent: Nov. 23, 2010

(54) ANTIBODIES TO TRAIN R: A CYSTEINE-RICH MEMBER OF THE TNF-RECEPTOR FAMILY, AND METHODS OF TREATING TUMORS EXPRESSING SAID RECEPTOR

(75) Inventors: Jurg Tschopp, Epalinges (CH); Catherine Hession, Hingham, MA (US)

(73) Assignees: Biogen Idec MA Inc., Cambridge, MA (US); Apoxis S.A., Epalinges (CH)

( * ) Notice: Subject to any disclaimer, the term of this patent is extended or adjusted under 35 U.S.C. 154(b) by 0 days.

(21) Appl. No.: 12/130,740

(22) Filed: May 30, 2008

(65) Prior Publication Data

US 2009/0004188 A1 Jan. 1, 2009

Related U.S. Application Data

(60) Division of application No. 11/396,907, filed on Apr. 4, 2006, now Pat. No. 7,402,658, which is a continuation of application No. 10/303,502, filed on Nov. 22, 2002, now Pat. No. 7,223,852, which is a continuation of application No. 09/522,436, filed on Mar. 9, 2000, now abandoned, which is a continuation-in-part of application No. PCT/US98/19030, filed on Sep. 11, 1998.

(60) Provisional application No. 60/084,422, filed on May 6, 1998, provisional application No. 60/058,631, filed on Sep. 12, 1997.

(51) Int. Cl.
*C12P 21/08* (2006.01)
*C07K 16/00* (2006.01)
*A61K 39/395* (2006.01)
*A61K 39/00* (2006.01)

(52) U.S. Cl. ............... 530/387.9; 530/387.1; 530/387.3; 530/388.1; 530/388.15; 530/388.22; 424/130.1; 424/133.1; 424/139.1

(58) Field of Classification Search ........................ None
See application file for complete search history.

(56) References Cited

U.S. PATENT DOCUMENTS

| 5,225,538 | A | 7/1993 | Capon et al. |
| 7,223,852 | B2 | 5/2007 | Tschopp et al. |
| 2002/0068696 | A1 | 6/2002 | Wood et al. |
| 2003/0027272 | A1 | 2/2003 | Baker et al. |
| 2004/0142423 | A1 | 7/2004 | Tada et al. |
| 2006/0058223 | A1 | 3/2006 | Mi et al. |
| 2006/0233792 | A1 | 10/2006 | Tschopp et al. |
| 2007/0186296 | A1 | 8/2007 | Gao et al. |

FOREIGN PATENT DOCUMENTS

| EP | 0 990 703 A1 | 4/2000 |
| WO | WO 94/04679 A1 | 3/1994 |
| WO | WO 98/01554 A3 | 1/1998 |
| WO | WO 99/11791 A2 | 3/1999 |
| WO | WO 99/11791 A3 | 3/1999 |
| WO | WO 99/13078 A1 | 3/1999 |
| WO | WO 99/20644 A1 | 4/1999 |
| WO | WO 99/33967 A2 | 7/1999 |
| WO | WO 99/33980 A2 | 7/1999 |
| WO | WO 99/37818 A1 | 7/1999 |
| WO | WO 00/01817 | 1/2000 |
| WO | WO 00/49149 A1 | 8/2000 |
| WO | WO 00/53758 A2 | 9/2000 |
| WO | WO 01/38526 A2 | 5/2001 |
| WO | WO 01/58954 A3 | 8/2001 |
| WO | WO 01/68848 A2 | 9/2001 |
| WO | WO 01/93983 A1 | 12/2001 |
| WO | WO 02/00690 A2 | 1/2002 |
| WO | WO 02/08284 | 1/2002 |
| WO | WO 02/08288 A2 | 1/2002 |
| WO | WO 03/013578 A1 | 2/2003 |
| WO | WO 2005/058028 A2 | 6/2005 |
| WO | WO 2006/017673 A2 | 2/2006 |

OTHER PUBLICATIONS

NCBI Entrez, Accession No. AAK28396, Chaudhary, D. and Long A.J. (Apr. 2, 2001).
NCBI Entrez, Accession No. Q9NS68, Eby, M.T., et al. (May 30, 2002).
NCBI Entrez, Accession No. NM_148957, Clark, H.F., et al. (Sep. 20, 2002).
NCBI Entrez, Accession No. AY358888, Clark, H.F., et al. (Oct. 1, 2003).
NCBI Entrez, Accession No. CAH70838, Pearce, A. (Nov. 9, 2004).
NCBI Entrez, Accession No. BC047321, Strausberg, R.L., et al. (Mar. 3, 2003).
NCBI Entrez, Accession No. AAF71828, Eby, M.T., et al. (May 25, 2000).
Pan, G., et al., "An Antagonist Decoy Receptor and a Death Domain-Containing Receptor for TRAIL," *Science* 277:815-818, American Association for the Advancement of Science (Aug. 1997).
Sheridan, J.P., et al., "Control of TRAIL-Induced Apoptosis by a Family of Signaling and Decoy Receptors," *Science* 277:818-821, American Association for the Advancement of Science (Aug. 1997).
Aggarwal et al., "Tumor Necrosis Factors: Developments During the Last Decade," *Eur. Cytokine Netw,* 7:93-124, John Libbey Eurotext, Ltd. (Apr.-Jun. 1996).

(Continued)

*Primary Examiner*—Robert Landsman
(74) *Attorney, Agent, or Firm*—Sterne, Kessler, Goldstein & Fox PLLC

(57) ABSTRACT

Embodiments of the present invention encompass novel receptors of the TNF family. In particular, embodiments of the invention encompass TNF Receptor in the BRAIN (TRAIN) and isolated antibodies that bind to the same. In some embodiments, isolated antibodies that bind to TRAIN are useful in regulating cell differentiation, death, and survival. Other embodiments of the invention encompass pharmaceutical compositions comprising antibodies that bind to human TRAIN.

11 Claims, 5 Drawing Sheets

OTHER PUBLICATIONS

Banner, D.W., et al., "Crystal Structure of the Soluble Human 55 kd TNF Receptor-Human TNFβ Complex: Implications for TNF Receptor Activation," *Cell 73:*431-445, Cell Press (1993).

Bazzoni et al., "The Tumor Necrosis Factor Ligand and Receptor Families," *N Engl. J. Med.,* 334:1717-1725, Massachusetts Medical Society (Jun. 1996).

Bodmer, J.L., et al., "The molecular architecture of the TNF superfamily," *Trends Biomed. Sci. 27:*19-26, Elsevier Science Ltd. (Jan. 2002).

Bork, et al., "Go Hunting in Sequence Databases But Watch Out for the Traps," *Trends in Genetics* 12:425-427, Elsevier Science Ltd. (Oct. 1996).

Bork, "Powers and Pitfalls in Sequence Analysis: The 70% Hurdle," *Genome Res.* 10:398-400, Cold Spring Harbor Laboratory Press (Apr. 2000).

Brenner SE., "Errors in Genome Annotation," *Trends in Genetics* 15:132-133, Elsevier Science Ltd. (Apr. 1999).

Doerks, T., et al., "Protein Annotation: Detective Work for Function Prediction," *Trends in Genetics* 14:248-250, Elsevier Science Ltd. (1998).

Eason et al., "Evaluation of Recombinant Human Soluble Dimeric Tumor Necrosis Factor Receptor for Prevention of OKT3-associated Acute Clinical Syndrome," *Transplantation,* 61:224-228, Lippincott Williams & Wilkins (Jan. 1996).

Eby, M.T., et al., "TAJ, a Novel Member of the Tumor Necrosis Factor Receptor Family, Activates the c-Jun N-terminal Kinase Pathway and Mediates Caspase-independent Cell Death," *J. Biol. Chem. 275:*15336-15342, The American Society for Biochemistry and Molecular Biology, Inc. (May 2000).

Eggermont et al., "Isolated Limb Perfusion with High-Dose Tumor Necrosis Factor-Alpha in Combination with Interferon-Gamma and Melphalan for Nonresectable Extremity Soft Tissue Sarcomas: A Multicenter Trial," *J. Clin. Oncol.,* 14:2653-2665, American Society of Clinical Oncology (Oct. 1996).

Feldmann et al., "Role of Cytokines in Rheumatoid Arthritis," *Ann. Rev. Immunol.,* 14:397-440, Elsevier Science Ltd. (Apr. 1996).

Green et al., "Fas-Ligand: Privilege and Peril.," *Proc. Natl. Acad. Sci. USA,* 94:5986-5990, National Academy of Sciences (Jun. 1997).

Hisaoka, T., et al., "Expression of a member of tumor necrosis factor receptor superfamily, TROY, in the developing mouse brain," *Develop. Brain Res. 143:*105-109, Elsevier Science B.V. (Jun. 2003).

Kojima, T., et al., "TROY, a Newly Identified Member of the Tumor Necrosis Factor Receptor Superfamily, Exhibits a Homology with Edar and Is Expressed in Embryonic Skin and Hair Follicles," *J. Biol. Chem. 275:*20742-20747, The American Society for Biochemistry and Molecular Biology, Inc. (Jul. 2000).

Mandemakers, W.J. and Barres, B.A., "Axon Regeneration: It's Getting Crowded at the Gates of TROY," *Curr. Biol. 15:*R302-R305, Cell Press (Apr. 2005).

Mikayama et al., "Molecular Cloning and Functional Expression of a Cdna Encoding Glycosylation-Inhibiting Factor," *Proc. Natl. Acad. Sci. USA,* 90:10056-10060, National Academy of Sciences (1993).

Robertson, N.G., et al., "Isolation of Novel and Known Genes from a Human Fetal Cochlear cDNA Library Using Subtractive Hybridization and Differential Screening," *Genomics 23:*42-50, Academic Press, Inc. (1994).

Shao, Z., et al., "TAJ/TROY, an Orphan TNF Receptor Family Member, Binds Nogo-66 Receptor 1 and Regulates Axonal Regeneration," *Neuron 45:*353-359, Elsevier Inc. (Feb. 2005).

Skolnick et al., "From Genes to Proteins Structure and Function: Novel Applications of Computational Approaches in the Genomic Area," *Trends Biotechnol.,* 18:34-39, Elsevier Science Ltd. (Jan. 2000).

Smith et al., "CD30 Antigen, a marker for Hodgkin's Lymphoma, is a Receptor Whose Ligand Defines an Emerging Family of Cytokines with Homology to TNF," *Cell,* 73:1349-1360, Cell Press (1993).

Smith, "Virus Strategies for Evasion of the Host Response to Infection," *Trends Microbiol.,* 2:81-88, Elsevier Science Ltd. (1994).

Smith et al., "The TNF Receptor Superfamily of Cellular and Viral Proteins: Activation, Costimulation, and Death," *Cell,* 76:959-962, Cell Press (1994).

Smith, T.F., et al., "The Challenges of Genome Sequence Annotation or the Devil is in the Details," *Nat. Biotechnol. 15:*1222-1223, Nature Publishing Group (Nov. 1997).

Van Dullemen et al., "Treatment of Crohn's Disease with Anti-Tumor Necrosis Factor Chimeric Monoclonal Antibody (cA2)," *Gastroenterology,* 109:129-135, W.B. Saunders (1995).

Wang, Y., et al., "An Alternative Form of Paraptosis-Like Cell Death, Triggered by TAJ/TROY and Enhanced by PDCD5 Overexpression," *J. Cell Sci. 117:*1525-1532, The Company of Biologists (Mar. 2004).

Wilson, C.A., et al. "Death of HT29 adenocarcinoma cells induced by TNF family receptor activation is caspase-independent and displays features of both apoptosis and necrosis," *Cell Death Diff. 9:*1321-1333, Nature Publishing Group (Dec. 2002).

NCBI Entrez, Accession No. NP_061117, Clark, H.F., et al. (Jul. 5, 2000).

NCBI Entrez, Accession No. BAB03269, Kojima, T., et al. (Jul. 22, 2000).

```
   1  GAATTCCGGG GGAGGTGCAC GGTGTGCACG CTGGACTGGA CCCCCCATGC
  51  AACCCCGCGC CCTGCGCCTT AACCAGGACT GCTCCGCGCG CCCCTGAGCC
 101  TCGGGCTCCG GCCCGGACCT GCAGCCTCCC AGGTGGCTGG GAAGAACTCT
 151  CCAACAATAA ATACATTTGA TAAGAAAGAT GGCTTTAAAA GTGCTACTAG
 201  AACAAGAGAA AACGTTTTTC ACTCTTTTAG TATTACTAGG CTATTTGTCA
 251  TGTAAAGTGA CTTGTGAATC AGGAGACTGT AGACAGCAAG AATTCAGGGA
 301  TCGGTCTGGA AACTGTGTTC CCTGCAACCA GTGTGGGCCA GGCATGGAGT
 351  TGTCTAAGGA ATGTGGCTTC GGCTATGGGG AGGATGCACA GTGTGTGACG
 401  TGCCGGCTGC ACAGGTTCAA GGAGGACTGG GGCTTCCAGA AATGCAAGCC
 451  CTGTCTGGAC TGCGCAGTGG TGAACCGCTT TCAGAAGGCA AATTGTTCAG
 501  CCACCAGTGA TGCCATCTGC GGGGACTGCT TGCCAGGATT TTATAGGAAG
 551  ACGAAACTTG TCGGCTTTCA AGACATGGAG TGTGTGCCTT GTGGAGACCC
 601  TCCTCCTCCT TACGAACCGC ACTGTGCCAG CAAGGTCAAC CTCGTGAAGA
 651  TCGCGTCCAC GGCCTCCAGC CCACGGGACA CGGCGCTGGC TGCCGTTATC
 701  TGCAGCGCTC TGGCCACCGT CCTGCTGGCC CTGCTCATCC TCTGTGTCAT
 751  CTATTGTAAG AGACAGTTTA TGGAGAAGAA ACCCAGCTGG TCTCTGCGGT
 801  CGCAGGACAT TCAGTACAAC GGCTCTGAGC TGTCGTGTTT TGACAGACCT
 851  CAGCTCCACG AATATGCCCA CAGAGCCTGC TGCCAGTGCC GCCGTGACTC
 901  AGTGCAGACC TGCGGGCCGG TGCGCTTGCT CCCATCCATG TGCTGTGAGG
 951  AGGCCTGCAG CCCCAACCCG GCGACTCTTG GTTGTGGGGT GCATTCTGCA
1001  GCCAGTCTTC AGGCAAGAAA CGCAGGCCCA GCCGGGGAGA TGGTGCCGAC
1051  TTTCTTCGGA TCCCTCACGC AGTCCATCTG TGGCGAGTTT TCAGATGCCT
1101  GGCCTCTGAT GCAGAATCCC ATGGGTGGTG ACAACATCTC TTTTTGTGAC
1151  TCTTATCCTG AACTCACTGG AGAAGACATT CATTCTCTCA ATCCAGAACT
1201  TGAAAGCTCA ACGTCTTTGG ATTCAAATAG CAGTCAAGAT TTGGTTGGTG
1251  GGGCTGTTCC AGTCCAGTCT CATTCTGAAA ACTTTACAGC AGCTACTGAT
1301  TTATCTAGAT ATAACAACAC ACTGGTAGAA TCAGCATCAA CTCAGGATGC
1351  ACTAACTATG AGAAGCCAGC TAGATCAGGA GAGTGGCGCT GTCATCCACC
1401  CAGCCACTCA GACGTCCCTC CAGGAAGCTT AAAGAACCTG CTTCTTTCTG
1451  CAGTAGAAGC GTGTGCTGGA ACCCAAAGAG TACTCCTTTG TTAGGCTTAT
1501  GGACTGAGCA GTCTGGACCT TGCATGGCTT CTGGGGCAAA AATAAATCTG
1551  AACCAAACTG ACGGCATTTG AAGCCTTTCA GCCAGTTGCT TCTGAGCCAG
1601  ACCAGCTGTA AGCTGAAACC TCAATGAATA ACAAGAAAAG ACTCCAGGCC
1651  GACTCATGAT ACTCTGCATC TTTCCTACAT GAGAAGCTTC TCTGCCACAA
1701  AAGTGACTTC AAAGACGGAT GGGTTGAGCT GGCAGCCTAT GAGATTGTGG
1751  ACATATAACA AGAAACAGAA ATGCCCTCAT GCTTATTTTC ATGGTGATTG
1801  TGGTTTTACA AGACTGAAGA CCCAGAGTAT ACTTTTTCTT TCCAGAAATA
1851  ATTTCATACC GCCTATGAAA TATCAGATAA ATTACCTTAG CTTTTATGTA
1901  GAATGGGTTC AAAAGTGAGT GTTTCTATTT GAGAAGGACA CTTTTTCATC
1951  ATCTAAACTG ATTCGCATAG GTGGTTAGAA TGGCCCTCAT ATTGCCTGCC
2001  TAAATCTTGG GTTTATTAGA TGAAGTTTAC TGAATCAGAG GAATCAGACA
2051  GAGGAGGATA GCTCTTTCCA GAATCCACAC TTCTGACCTC AGCCTCGGTC
2101  TCATGAACAC CCGCTGATCT CAGGAGAACA CCTGGGCTAG GGAATGTGGT
2151  CGAGAAAGGG CAGCCCATTG CCCAGAATTA ACACA
```

FIG. 1

```
         Gap Weight:   3.000       Average Match:    0.540
      Length Weight:   0.100    Average Mismatch:   -0.396

Quality: 272.2              Length:    214
               Ratio:   1.272              Gaps:      0
  Percent Similarity:  86.449    Percent Identity:  81.776

1 MALKVLLEQEKTFFTLLVLLGYLSCKVTCESGDCRQQEFRDRSGNCVPCN  50
     ||||||  : ..:|. :::|  .|.|||.||.||||||||:||||||| |.
   1 MALKVLPLHRTVLFAAILFLLHLACKVSCETGDCRQQEFKDRSGNCVLCK  50

51 QCGPGMELSKECGFGYGEDAQCVTCRLHRFKEDWGFQKCKPCLDCAVVNR 100
     |||||||||||||||||||||||.|| |||||||||||||||| |||:|||
  51 QCGPGMELSKECGFGYGEDAQCVPCRPHRFKEDWGFQKCKPCADCALVNR 100

101 FQKANCSATSDAICGDCLPGFYRKTKLVGFQDMECVPCGDPPPPYEPHCA 150
     ||:|||| ||||:|||||||||||||||||||||||||||||||||||||.
 101 FQRANCSHTSDAVCGDCLPGFYRKTKLVGFQDMECVPCGDPPPPYEPHCT 150

151 SKVNLVKIASTASSPRDTALAAVICSALATVLLALLILCVIYCKRQFMEK 200
     ||||||||.||.||||||||||||||||||||||||||||||||||||||
 151 SKVNLVKISSTVSSPRDTALAAVICSALATVLLALLILCVIYCKRQFMEK 200

201 KPSWSLRSQDIQYN 214
     ||| .|.|  :  .
 201 KPSCKLPSLCLTVK 214
```

FIG. 2

```
  1  GAATTCCAAA TGCTAAAACC TAGTTCTTTA TTCATCTATA AGGTATTTTG
 51  TCGTTTAAGT TTCAATAAAA ATGCCGAAGA CCACTGACTT TATATTCCCC
101  CACCTGCACC CCCACCCCAA TATAGAAGAA GTGCACTGAG AAGCATCTGC
151  AAAGTTAGCT TTAGGGGAAT TGATATTTCT TAAGTGTCCA CTGCTTCCTC
201  TTCAAAAATG TGTCTACCTA AGATACTATT ATTTAAGCCT CTGTGTACTT
251  TTAACCGTAG AACTGGTAAT GGAGACTGCT GGTAATTTAT GACCACAACT
301  GTAAGCTTAG ATGAAAGAGT TAACAAGGAG TATTTTCCTT TCTCTTCTAG
351  ATTTTATAGG AAGACGAAAC TTGTCGGCTT TCAAGACATG GAGTGTGTGC
401  CTTGTGGAGA CCCTCCTCCT CCTTACGAAC CGCACTGTGA GTGAACGCAA
451  CACAGGCAGA GCCAAGGGGA CGCCTGGCCT TTTGAAAAAG TTTAAATTTG
501  TAAACGTTTC TTCTCTGGCA GATGGAGCCA AATCTGTCTC TCCTGTGGGG
551  TGTACAGTGT GTCCTCTTTA ATCAGGCTTC TGGCAGGACA GAAAGTCCCT
601  TTGTTCTGTG CCTCAGTCAG CAAACCGGTC CCAGGGATTT GAATCTCAGA
651  GTGGAGTGCA GACATTTTGC CACTGCTCAG CTCCTTCTGA AGCCTTCCCT
701  GGCACCCTGG GTCTGTAATT CAGGCCACTT TGAATAACCA GGCGGCTCAC
751  ATCCTCACTC TTAGGTCTTC GTGCCCTGGC CCATGAATT C
```

MALKVLLEQEKTFFTLLVLLGYLSCKVTCESGDCRQQEFRDRSGNCVPCNQCGPGMELSKECGFGYGE
DAQCVTCRLHRFKEDWGFQKCKPCLDCAVVNRFQKANCSATSDAICGDCLPGFYRKTKLVGFQDMECV
PCGDPPPPYEPHCASKVNLVKIASTASSPRDTALAAVICSALATVLLALLILCVIYCKRQFMEKKPSW
SLRSQDIQYNGSELSCFDRPQLHEYAHRACCQCRRDSVQTCGPVRLLPSMCCEEACSPNPATLGCGVH
SAASLQARNAGPAGEMVPTFFGSLTQSICGEFSDAWPLMQNPMGGDNISFCDSYPELTGEDIHSLNPE
LESSTSIDSNSSQDLVGGAVPVQSHSENFTAATDLSRYNNTLVESASTQDALTMRSQLDQESGAVIHP
ATQTSLQEA

FIG 5

FYRKTKLVGFQDMECVPCGDPPPPYEPHCE

ANTIBODIES TO TRAIN R: A CYSTEINE-RICH MEMBER OF THE TNF-RECEPTOR FAMILY, AND METHODS OF TREATING TUMORS EXPRESSING SAID RECEPTOR

RELATED APPLICATIONS

This application is a divisional of application Ser. No. 11/396,907, filed Apr. 4, 2006, now issued U.S. Pat. No. 7,402,658, which is a continuation of application Ser. No. 10/303,502, filed Nov. 22, 2002, now issued U.S. Pat. No. 7,223,852, which is a continuation of application Ser. No. 09/522,436, filed Mar. 9, 2000, now abandoned, which is a continuation-in-part of International Application No. PCT/US98/19030, filed Sep. 11, 1998, which claims the benefit of application Ser. No. 60/084,422, filed May 6, 1998 and the benefit of application Ser. No. 60/058,631, filed Sep. 12, 1997, all of which are incorporated herein by reference in their entireties.

BACKGROUND OF THE INVENTION

The present invention relates to novel receptors in the TNF family. A novel receptor has been identified, referred to herein as TRAIN (TNF Receptor in the BRAIN).

The TNF family consists of pairs of ligands and their specific receptors referred to as TNF family ligands and TNF family receptors (Bazzoni and Beutler, 1996. N Engl J Med 334, 1717-25). The family is involved in the regulation of the immune system and possibly other non-immunological systems. The regulation is often at a "master switch" level such that TNF family signaling can result in a large number of subsequent events best typified by TNF. TNF can initiate the general protective inflammatory response of an organism to foreign invasion that involves the altered display of adhesion molecules involved in cell trafficking, chemokine production to drive specific cells into specific compartments and the priming of various effector cells. As such, the regulation of these pathways has clinical potential.

The TNF receptor family is a collection of related proteins that generally consist of an extracellular domain, a transmembrane domain and an intracellular signaling domain. The extracellular domain is built from 2-6 copies of a tightly disulphide bonded domain and is recognized on the basis of the unique arrangement of cysteine residues. Each receptor binds to a corresponding ligand although one ligand may share several receptors. In some cases, it is clear that by alternate RNA splicing, soluble forms of the receptors lacking the transmembrane region and intracellular domain exist naturally. Moreover, in nature, truncated versions of these receptors exist and the soluble inhibitory form may have direct biological regulatory roles. Clearly, viruses have used this tactic to inhibit TNF activity in their host organisms (Smith, 1994. Trends in Microbiol. 82, 81-88). These receptors can signal a number of events including cell differentiation, cell death or cell survival signals. Cell death signaling often is triggered via relatively direct links to the caspase cascade of proteases e.g. Fas and TNF receptors. Most receptors in this class can also activate NFKB controlled events.

An emerging theme in the TNF family of receptors has been the use by nature of both full length receptors with intracellular domains that transmit a signal and alternate forms which are either secreted or lack an intracellular signaling domain. These later forms can inhibit ligand signaling and hence can dampen a biological response. There are several examples of this phenomenon. First, the TNF receptor p75 is readily secreted following selective cleavage from the membrane and then acts to block the action of TNF. It is likely that nature has evolved this system to buffer TNF activity. A second example is provided by the TRIAL-TRAIL receptor system where there are 4 separate genes encoding TRAIL receptors. Two of these TRAIL-R1 and TRAIL-R2 possess intracellular domains and transduce signal. A third receptor (TRAIL-R4) has an intracellular domain yet this domain does not have all the elements is found in R1 and R2, e.g. it lacks a domain capable of signaling cell death. Lastly, there is a fourth receptor TRAIL-R3, that is essentially a soluble form but remains tethered by a glycolipid linkage. Hence this receptor can bind ligand yet it is unable to transmit a signal, i.e. it is effectively a decoy receptor. A third example is provided by the osteoprotegerin (OPG) system where the OPG receptor lacks a transmembrane domain and is secreted into the medium. This receptor can block the signaling necessary to induce osteoclast differentiation possibly by binding to a ligand called RANK-L. The TRAIN system described here resembles the OPG paradigm in that a short version can be secreted that would inhibit the natural TRAIN-L (currently unknown) from binding to full length TRAIN and eliciting a signal.

The receptors are powerful tools to elucidate biological pathways via their easy conversion to immunoglobulin fusion proteins. These dimeric soluble receptor forms are good inhibitors of events mediated by either secreted or surface bound ligands. By binding to these ligands they prevent the ligand from interacting with cell associated receptors that can signal. Not only are these receptor-Ig fusion proteins useful in an experimental sense, but they have been successfully used clinically in the case of TNF-R-Ig to treat inflammatory bowel disease, rheumatoid arthritis and the acute clinical syndrome accompanying OKT3 administration (Eason et al., 1996. Transplantation 61, 224-8; Feldmann et al., 1996. Annu Rev Immunol; van Dullemen et al., 1995. Gastroenterology 109, 129-35). One can envision that manipulation of the many events mediated by signaling through the TNF family of receptors will have wide application in the treatment of immune based diseases and also the wide range of s human diseases that have pathological sequelae due to immune system involvement. A soluble form of a recently described receptor, osteoprotegerin, can block the loss of bone mass and, therefore, the events controlled by TNF family receptor signaling are not necessarily limited to immune system regulation. Antibodies to the receptor can block ligand binding and hence can also have clinical application. Such antibodies are often very long-lived and may have advantages over soluble receptor-Ig fusion proteins which have shorter blood half-lives.

While inhibition of the receptor mediated pathway represents the most exploited therapeutic application of these receptors, originally it was the activation of the TNF receptors that showed clinical promise (Aggarwal and Natarajan, 1996. Eur Cytokine Netw 7, 93-124). Activation of the TNF receptors can initiate cell death in the target cell and hence the application to tumors was and still is attractive (Eggermont et al., 1996. J Clin Oncol 14, 2653-65). The receptor can be activated either by administration of the ligand, i.e. the natural pathway or some antibodies that can crosslink the receptor are also potent agonists. Antibodies would have an advantage in oncology since they can persist in the blood for long periods whereas the ligands generally have short lifespans in the blood. As many of these receptors may be expressed more selectively in tumors or they may only signal cell death or differentiation in tumors, agonist antibodies could be good weapons in the treatment of cancer. Likewise, many positive immunological events are mediated via the TNF family receptors, e.g. host inflammatory reactions, antibody production etc. and therefore agonistic antibodies could have beneficial effects in other, non-oncological applications.

Paradoxically, the inhibition of a pathway may have clinical benefit in the treatment of tumors. For example the Fas ligand is expressed by some tumors and this expression can lead to the death of Fas positive lymphocytes thus facilitating the ability of the tumor to evade the immune system. In this case, inhibition of the Fas system could then allow the immune system to react to the tumor in other ways now that access is possible (Green and Ware, 1997. Natl. Acad. Sci. USA 94, 5986-5990).

The receptors are also useful to discover the corresponding ligand as they can serve as probes of the ligand in expression cloning techniques (Smith et al., 1993. Cell 73, 1349-60). Likewise, the receptors and ligands can form in vitro binding assays that will allow the identification of inhibitory substances. Such substances can form the basis of novel inhibitors of the pathways.

BRIEF DESCRIPTION OF THE FIGURES

FIG. 1 shows the nucleotide sequence for human TRAIN receptor (SEQ ID NO: 7) from a composite of two lambda gt10 clones (GJ159 and GJ158).

FIG. 2 shows a comparison of human TRAIN receptor (top) (amino acids 1-214 of SEO ID NO: 3) and murine TRAIN receptor long (bottom) (SEQ ID NO: 2).

FIG. 3 shows the nucleotide sequences for human TRAIN receptor from a subclone of lambda gt10 cDNA (SEQ ID NO: 8).

FIG. 4 shows the amino acid sequence for human TRAIN (SEQ ID NO: 3) corresponding to the nucleotide sequence in FIG. 1.

FIG. 5 shows the amino acid sequence for human TRAIN (SEQ ID NO: 4) corresponding to the nucleotide sequence in FIG. 3.

A. DEFINITIONS

"Homologous", as used herein, refers to the sequence similarity between sequences of molecules being compared. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

A "purified preparation" or a "substantially pure preparation" of a polypeptide, as used herein, means a polypeptide that has been separated from other proteins, lipids, and nucleic acids with which it naturally occurs. Preferably, the polypeptide is also separated from other substances, e.g., antibodies, matrices, etc., which are used to purify it.

"Transformed host" as used herein is meant to encompass any host with stably integrated sequence, i.e. TRAIN sequence, introduced into its genome or a host possessing sequence, i.e. receptor encoding episomal elements.

A "treatment", as used herein, includes any therapeutic treatment, e.g., the administration of a therapeutic agent or substance, e.g., a drug.

A "substantially pure nucleic acid", e.g., a substantially pure DNA, is a nucleic acid which is one or both of: (1) not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding TRAIN.

The terms "peptides", "proteins", and "polypeptides" are used interchangeably herein.

"Biologically active" as used herein, means having an in vivo or in vitro activity which may be performed directly or indirectly. Biologically active fragments of TRAIN may have, for example, 70% amino acid homology with the active site of the receptor, more preferably at least 80%, and most preferably, at least 90% homology. Identity or homology with respect to the receptor is defined herein as the percentage of amino acid residues in the candidate sequence which are identical to the TRAIN residues in SEQ. ID. NO. 3.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature.

The claimed invention relates to a novel receptor designated TRAIN-R. The amino acid sequence of murine TRAIN-R is set forth in SEQ. I). NO. 1 (the short form) and SEQ. ID. NO. 2, (the long form). The full length amino acid sequence of human TRAIN-R is set forth in SEQ. ID. NO. 3 and FIG. 1. As shown in FIG. 1, the protein length is 417 amino acids. The predicted signal sequence runs from residues 1-25. It is believed that the mature N-terminus is at amino acid residue 26, the extracellular domain spans residues 26-173, the transmembrane domain spans residues 174-190, and the cytoplasmic domain spans residues 191-417. There is a potential N-linked glycosylation site at residue 105.

SEQ. ID. NO. 4 sets forth the amino acid sequence for the carboxy terminal 30 amino acids of a secreted form of human TRAIN-R from a subclone of lambda gt10 cDNA (GJ156). This peptide sequence features 30 amino acids that are identical to amino acids 121-149 of the composite protein shown in FIG. 1 and are identical to amino acids 121-150 of the C-terminus of murine TRAIN-R short form (secreted protein). SEQ. ID. NO 9 shows the amino acid sequence of the entire short secreted form of the human TRAIN-R based on the alternate cloned exon and by comparison to the mouse short form.

FIG. 2 shows a comparison of the first 214 amino acids of human TRAIN-R (417 a.a.) and murine TRAIN-R long (214 a.a.). As shown in the Figure, the two sequences have an identity of about 81.8%.

The TRAIN receptors of the invention may be isolated from mammalian tissues and purified to homogeneity, or isolated from cells which contain membrane-bound TRAIN-R, and purified to homogeneity. Methods for growing cells and isolating cell extracts are well known in the art, as are various cell types and growth and isolation methods. In general, any TRAIN-R can be isolated from any cell or tissue expressing this protein using a cDNA probe, isolating MRNA and transcribing the mRNA into cDNA. Thereafter, the protein can be produced by inserting the cDNA into an expression vector, such as a virus, plasmid, cosmid or other expression vector, inserting the expression vector into a cell, and proliferating the resulting cells. The TRAIN-R can then be isolated from the medium or cell extract by methods well known in the art. One skilled in the art can readily vary the vectors and cell lines and still obtain the claimed receptors. Alternatively, TRAIN receptors can be chemically synthesized using the sequences set forth in SEQ. ID. NOs. 1, 2, 3 or 4.

It is believed that murine TRAIN-R is expressed highest in brain and lung and at a lower level in liver, skeletal muscle and kidney. The expression pattern of human TRAIN-R differs in that a low level of expression has been detected in every tissue and cell line tested thus far (ubiquitous) with a significantly higher expression detected in heart, prostate, ovary, testis, peripheral blood lymphocytes (PBLs), thyroid, and adrenal gland.

Murine TRAIN-R may exist in nature as a natural soluble form as indicated in SEQ. ID. NO. 1. Human TRAIN-R may exist as a natural soluble form having the carboxy sequence indicated in SEQ. ID. NO. 4 and FIG. 3. The soluble protein should inhibit signaling by the full length TRAIN-R.

The present invention also encompasses DNA sequences which encode the murine (both long and short) and human TRAIN receptors (full length and carboxy terminus). These DNA sequences are set forth in SEQ. ID. NOs. 5, 6, 7 and 8, respectively. The human TRAIN-R sequence in SEQ. ID. NO. 7 contains 5'UTR, a complete coding region, a stop codon and some 3'UTR. FIG. 1 shows the nucleotide sequence for human TRAIN-R as derived from a composite sequence of GJ159 and GJ158. As shown in FIG. 1, human TRAIN-R has a nucleotide sequence length of 2185, a coding region from 179-1429, and a stop codon at 1430-1432.

The human TRAIN-R sequence in SEQ. ID. NO. 8 contains intron sequence, an exon encoding the carboxy terminal 30 amino acids of a secreted form of human TRAIN-R, a stop codon and 3'UTR. As shown in FIG. 3, it is believed that the intron is at residues 1-350, the coding region at 352-441, the stop codon at 442-444 and the 3'UTR=445-791.

In other embodiments, the invention relates to sequences that have at least 50% homology with DNA sequences encoding the C terminal receptor binding domain of the ligands and hybridize to the claimed DNA sequences or fragments thereof, and which encode the TRAIN receptors having the sequences identified in SEQ. ID. NO. 1, 2,3 or4.

The invention in certain embodiments furthermore relates to DNA sequences encoding the TRAIN receptors where the sequences are operatively linked to an expression control sequence. Any suitable expression control sequences are useful in the claimed invention, and can easily be selected by one skilled in the art.

The invention also contemplates recombinant DNAs comprising a sequence encoding TRAIN receptors or fragments thereof, as well as hosts with stably integrated TRAIN-R sequences introduced into their genome, or possessing episomal elements. Any suitable host may be used in the invention, and can easily be selected by one skilled in the art without undue experimentation.

The claimed invention in certain embodiments encompasses recombinant TRAIN-R. One skilled in the art can readily isolate such recombinant receptors thereby providing substantially pure recombinant TRAIN-R polypeptides. Isolated receptors of the invention are substantially free of other contaminating materials of natural or endogenous origin, and contain less than about 10-15% by mass of protein contaminants residual of production processes.

Mammalian Receptors within the scope of the invention also include, but are not limited to, primate, human, murine, canine, feline, bovine, ovine, equine and porcine TRAIN-R. Mammalian Receptors can also be obtained by cross species hybridization using a single stranded cDNA derived from the human TRAIN-R. DNA sequences of the invention can be used as a hybridization probe to isolate Receptor cDNAS from other mammalian cDNA libraries.

Derivatives of the Receptors within the scope of the invention also include various structural forms of the proteins of SEQ. ID. NOs. 1, 2, 3 and 4 which retain biological activity. For example, a receptor protein may be in the form of acidic or basic salts, or may be in neutral form. Individual amino acid residues may also be modified by oxidation or reduction.

Receptor derivatives may also be used as immunogens, reagents in a receptor-based immunoassay, or as binding agents for affinity purification procedures of TRAIN ligands.

The present invention also includes TRAIN-R with or without associated native-pattern glycosylation. One skilled in the art will understand that the glycosylation pattern on the receptor may vary depending on the particular expression system used. For example, typically, expression in bacteria such as *E. coli* results in a non-glycosylated molecule. TRAIN-R derivatives may also be obtained by mutations of the receptors or their subunits. A mutant, as referred to herein, is a polypeptide homologous to a claimed Receptor but which has an amino acid sequence different from the native sequence due to a deletion, insertion or substitution.

Bioequivalent analogs of the Receptor proteins of the invention may be constructed by, for example, making various substitutions of residues or sequences or deleting terminal or internal residues or sequences not needed for biological activity. For example, often cysteine residues can be deleted or replaced with other amino acids to prevent formation of unnecessary or incorrect intramolecular disulfide bridges upon renaturation. Other approaches to mutagenesis involved modifications, for example, to enhance expression in the chosen expression system.

Soluble Receptors of the invention may comprise subunits which have been changed from a membrane bound to a soluble form. Thus, soluble peptides may be produced by truncating the polypeptide to remove, for example, the cytoplasmic tail and/or transmembrane region. Alternatively, the transmembrane domain may be inactivated by deletion, or by substitutions of the normally hydrophobic amino acid residues which comprise a transmembrane domain with hydrophilic ones. In either case, a substantially hydrophilic hydropathy profile is created which will reduce lipid affinity and improve aqueous solubility. Deletion of the transmembrane domain is preferred over substitution with hydrophilic amino acid residues because it avoids introducing potentially immunogenic epitopes. Soluble Receptors of the invention may include any number of well-known leader sequences at the N-terminus. Such a sequence would allow the peptides to be expressed and targeted to the secretion pathway in a eukaryotic system.

The invention herein provides agents, such as agonists and antagonists, directed against the claimed receptors. In certain embodiments of this invention, the agent comprises a blocking agent that comprises and antibody directed against the TRAIN-R that inhibits TRAIN receptor signaling. Preferably the antibody is a monoclonal antibody. Similarly, the claimed invention encompasses antibodies and other agents which act as agonists in the TRAIN pathways.

Inhibitory anti-TRAIN-R antibodies and other receptor blocking agents can be identified using screening methods that detect the ability of one or more agents either to bind to the TRAIN-R, or ligands thereto, or to inhibit the effects of TRAIN-R signaling on cells.

One skilled in the art will have knowledge of a number of assays that measure the strength of ligand-receptor binding and can be used to perform competition assays with putative TRAIN receptor blocking agents. The strength of the binding between a receptor and ligand can be measured using an enzyme-linked immunoadsorption assay (ELISA) or a radioimmunoassay (RIA). Specific binding may also be measured by flourescently labeling antibody-antigen complexes and performing fluorescence activated cell sorting analysis (FACS), or by performing other such immunodetection methods, all of which are techniques well-known in the art.

With any of these or other techniques for measuring receptor-ligand interactions, one skilled in the art can evaluate the ability of a blocking agent, alone or in combination with other agents, to inhibit binding of ligands to the receptor molecules. Such assays may also be used to test blocking agents or derivatives of such agents, i.e. fusions, chimeras, mutants or chemically altered forms, to optimize the ability of the agent to block receptor activation.

The receptor blocking agents of the invention in one embodiment comprise soluble TRAIN receptor molecules. Using the sequence information herein and recombinant DNA techniques well known in the art, functional fragments encoding the TRAIN receptor ligand binding domain can be cloned into a vector and expressed in an appropriate host to produce a soluble receptor molecule. Soluble TRAIN receptor molecules that can compete with native TRAIN receptors for ligand binding according to the assays described herein can be selected as TRAIN receptor blocking agents.

A soluble TRAIN receptor comprising amino acid sequences selected form those shown herein may be attached to one or more heterologous protein domains ("fusion domains") to increase the in vivo stability of the receptor fusion protein, or to modulate its biological activity or localization.

Preferably, stable plasma proteins—which typically have a half-life greater than 20 hours in the circulation of a mammal—are used to construct the receptor fusion proteins. Such plasma proteins include but are not limited to: immunoglobulins, serum albumin, lipoproteins, apolipoproteins and transferrin. Sequences that can target the soluble receptors to a particular cell or tissue type may also be attached to the receptor ligand binding domain to create a specifically localized soluble receptor fusion protein.

All or a functional fragment of the TRAIN receptor extracellular region comprising the TRAIN receptor ligand binding domain may be fused to an immunoglobulin constant region like the Fc domain of a human IgG1 heavy chain. Soluble receptor-IgG fusions proteins are common immunological reagents and methods for their construction are well known in the art. (see, e.g. U.S. Pat. No. 5,225,538).

A functional TRAIN-R ligand binding domain may be fused to an immunoglobulin (Ig) Fc domain derived from an immunoglobulin class or subclass other than IgG1. The Fc domains of antibodies belonging to different Ig classes or subclasses can activate diverse secondary effector functions. Activation occurs when the Fc domain is bound by a cognate Fc receptor. Secondary effector functions include the ability to activate the complement system, to cross the placenta and to bind various microbial proteins. The properties of the different classes and subclasses of immunoglobulins are described in the art.

Activation of the complement system initiates cascades of enzymatic reactions that mediate inflammation. The products of the complement system have a variety of functions, including binding of bacteria, endocytosis, phagocytosis, cytotoxicity, free radical production and solubilization of immune complexes.

The complement enzyme cascade can be activated by the Fc domains of antigen-bound IgG1, IgG3 and Ig M antibodies. The Fc domain of IgG2 appears to be less effective, and the Fc domains of IgG4, IgA, IgD and IgE are ineffective at activating complement. Thus one can select an Fc domain based on whether its associated secondary effector functions are desirable for the particular immune response or disease being treated with the receptor-fusion protein.

It if would be advantageous to harm or kill the TRAIN ligand bearing target cell, one could, for example, select an especially active Fc domain (IgG1) to make the fusion protein. Alternatively, if it would be desirable to target the TRAIN receptor-FC fusion to a cell without triggering the complement system, an inactive IgG4 Fc domain could be selected.

Mutations in Fc domains that reduce or eliminate binding to Fc receptors and complement activation have been described in the art. These or other mutations can be used, alone or in combination to optimize the activity of the Fc domain used to construct the TRAIN receptor-Fc fusion protein.

One skilled in the art will appreciate that different amino acid residues forming the junction point of the receptor-Ig fusion protein may alter the structure, stability and ultimate biological activity of the soluble TRAIN receptor fusion protein. One or more amino acids may be added to the C-terminus of the selected TRAIN receptor fragment to modify the junction point whit the selected fusion domain.

The N-terminus of the TRAIN receptor fusion protein may also be varied by changing the position at which the selected TRAIN receptor DNA fragment is cleaved at its 5' end for insertion into the recombinant expression vector. The stability and activity of each TRAIN receptor fusion protein may be tested and optimized using routine experimentation and the assays for selecting blocking agents described herein.

Using the TRAIN receptor binding domain sequences within the extracellular domain as shown herein, amino acid sequence variants may also be constructed to modify the affinity of the soluble TRAIN receptor molecules for their ligands. The soluble molecules of this invention can compete for binding with endogenous receptors. It is envisioned that any soluble molecule comprising a TRAIN receptor ligand binding domain that can compete with native receptors for ligand binding is a receptor blocking agent that falls within the scope of the present invention.

In other embodiments of this invention, antibodies directed against the TRAIL and TRAIN receptors (anti-TRAIN-R abs) function as receptor blocking agents. The antibodies of this invention can be polyclonal or monoclonal and can be modified to optimize their ability to block TRAIN-R signaling, their bioavailability, stability or other desired traits.

Polyclonal antibody sera directed against TRAIN-R are prepared using conventional techniques by injecting animals such as goats, rabbits, rats, hamsters or mice subcutaneously with TRAIN-R-Fc fusion protein in Freund's adjuvant, followed by booster intraperitoneal or subcutaneous injection in incomplete Freund's. Polyclonal antisera containing the desired antibodies directed against the TRAIN receptors can then be screened by conventional immunological procedures.

Various forms of anti-TRAIN-R abs can also be made using standard recombinant DNA techniques. For example, "chimeric" antibodies can be constructed in which the antigen binding domain from an animal antibody is linked to a human constant domain. Chimeric antibodies reduce the observed immunogenic responses elicited by animal antibodies when used in human clinical treatments.

In addition, recombinant "humanized" antibodies which can recognize the TRAIN-R can be synthesized. Human antibodies are chimeras comprising mostly human IgG sequences into which the regions responsible for specific antigen-binding have been inserted. (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter species) sequences in human antibodies, and are less likely to elicit immune responses in the mammal being treated.

Construction of different classes of recombinant anti-TRAIN-R antibodies can also be accomplished by making chimeric or humanized antibodies comprising the anti-R variable domains and human constant domains isolated from different classes of immunoglobulins. For example, anti-TRAIN-R IgM antibodies with increased antigen binding site valencies can be recombinantly produced by cloning the antigen binding site into vectors carrying the human μ chain constant regions.

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling.

It may be desirable to increase or decrease the affinity of anti-TRAIN-R antibodies for the receptors depending on the targeted tissue type or the particular treatment schedule envisioned. For example, it may be advantageous to treat a patient with constant levels of anti-Receptor antibodies with reduced ability to signal through the pathway for semi-prophylactic treatments. Likewise, inhibitory anti-TRAIN-R antibodies with increased affinity for the receptors may be advantageous for short term treatments.

The claimed invention in yet other embodiments encompasses pharmaceutical compositions comprising an effective amount of a TRAIN-R blocking or activating agent, and pharmaceutically acceptable carriers. The compositions of the invention will be administered at an effective dose to treat the particular clinical condition addressed. Determination of a preferred pharmaceutical formulation and a therapeutically efficient dose regiment for a given application is well within the skill of the art taking into consideration for example, the condition and weight of the patient, the extent of desired treatment and the tolerance of the patient for the treatment. Doses of about 1 mg/kg of a soluble TRAIN-R are expected to be suitable starting points for optimizing treatment dosages.

Determination of a therapeutically effective dose can also be assessed by performing in vitro experiments that measure the concentration of the blocking or activating agent. The binding assays described herein are useful, as are other assays known in the art.

Administration of the soluble activating or blocking agents of the invention, alone or in combination, including isolated and purified forms, their salts, or pharmaceutically acceptable derivative thereof may be accomplished using any of the conventionally accepted modes of administration of agents which exhibit immunosuppressive activity.

EXAMPLES

Generation of Soluble Receptor Forms:

To form an receptor inhibitor for use in man, one requires the human receptor cDNA sequence of the extracellular domain. If the mouse form is known, human CDNA libraries can be easily screened using the mouse cDNA sequence and such manipulations are routinely carried out in this area. With a human cDNA sequence, one can design oligonucleotide primers to PCR amplify the extracellular domain of the receptor in the absence of the transmembrane and intracellular domains. Typically, one includes most of the amino acids between the last disulfide linked "TNF domain" and the transmembrane domain. One could vary the amount of "stalk" region included to optimize the potency of the resultant soluble receptor. This amplified piece would be engineered to include suitable restriction sites to allow cloning into various C-terminal Ig fusion chimera vectors. Alternatively, one could insert a stop signal at the 3' end and make a soluble form of the receptor without resorting to the use of a Ig fusion chimera approach. The resultant vectors can be expressed in most systems used in biotechnology including yeast, insect cells, bacteria and mammalian cells and examples exist for all types of expression. Various human Fc domains can be attached to optimize or eliminate FcR and complement interactions as desired. Alternatively, mutated forms of these Fc domains can be used to selectively remove FcR or complement interactions or the attachment of N-linked sugars to the Fc domain which has certain advantages.

Generation of Agonistic or Antagonistic Antibodies:

The above described soluble receptor forms can be used to immunize mice and to make monoclonal antibodies by conventional methods. The resultant mAbs that were identified by ELISA methods can be further screened for agonist activity either as soluble antibodies or immobilized on plastic in various in vitro cellular assays. Often the death of the HT29 cell line is a convenient system that is sensitive to signalling through many TNF receptors. If this line does not possess the receptor of interest, that full length receptor can be stably transfected into the HT29 line to now allow the cytotoxicity assay to work. Alternatively, such cells can be used in the Cytosensor apparatus to assess whether activation of the receptor can elicit a pH change that is indicative of a signalling event. TNF family receptors signal well in such a format and this method does not require one to know the actual biological events triggered by the receptor. The agonistic mAbs would be "humanized" for clinical use. This procedure can also be used to define antagonistic mAbs. Such mAbs would be defined by the lack of agonist activity and the ability to inhibit receptor-ligand interactions as monitored by ELISA, classical binding or BIAcore techniques. Lastly, the induction of chemokine secretion by various cells in response to an agonist antibody can form a screening assay.

Screening for Inhibitors of the Receptor-Ligand Interaction:

Using the receptor-Ig fusion protein, one can screen either combinatorial libraries for molecules that can bind the receptor directly. These molecules can then be tested in an ELISA formatted assay using the receptor-Ig fusion protein and a soluble form of the ligand for the ability to inhibit the receptor-ligand interaction. This ELISA can be used directly to screen various natural product libraries etc. for inhibitory compounds. The receptor can be transfected into a cell line such as the HT29 line to form a biological assay (in this case cytotoxicity) that can then form the screening assay.

It will be apparent to those skilled in the art that various modifications and variations can be made in the polypeptides, compositions and methods of the invention without departing from the spirit or scope of the invention. Thus, it is intended that the present invention cover the modifications and variations of this invention provided that they come within the scope of the appended claims and their equivalents.

Human TRAIN Receptor Identification:

Human TRAIN-R was cloned from two cDNA sequences. The first sequence (hTrainR) SEQ ID NO. 7 is a composite of two overlapping lambda gt10 clones (GJ159 and GJ158) from a Clontech Humann adult lung cDNA library. The composite sequence in SEQ. ID. NO. 7 is 2185 nucleotides in length and encodes a 417 amino acid protein (SEQ. ID. NO.3) which has a signal sequence, a 140 amino acid extracellular domain, a transmembrane domain and a 227 amino acid intracellular domain and a stop codon. The includes another 1200 bp. The extracellular domain of human TRAIN-R encodes three TNF receptor like domains (it appears to be missing domain 1 when compared to TNF-R). The sequence in SEQ. ID. NO. 3 is 19% identical to that of low affinity nerve growth factor (LNGFR) and 24% identical to Tramp/Lard4/Ws1/Dr3, both of which are members of the TNF family.

Human TRAIN-R was also cloned from a second sequence subclone of a lambda gt10 cDNA (GJ156, a 790 bp subclone). The resulting sequence is shown in SEQ. ID. NO. 8. It contains intron sequence, an exon encoding the Carboxy-terminal 30 amino acids of a secreted form of human TrainR, a stop codon and a 3'UTR. The 30 amino acids in the exon sequence were 100% homologous to the murine C-term secreted form (short form of murine Train Receptor).

Two predominant messages are observed 5 kb and 0.5 kb.

```
SEQ ID NO: 1
  1 MALKVLPLHR TVLFAAILFL LHLACKVSCE TGDCRQQEFK DRSGNCVLCK

51 QCGPGMELSK ECGFGYGEDA QCVPCRPHRF KEDWGFQKCK PCADCALVNR

101 FQRANCSHTS DAVCGDCLPG FYRKTKLVGF QDMECVPCGD PPPPYEPHCE

SEQ ID NO: 2
  1 MALKVLPLHR TVLFAAILFL LHLACKVSCE TGDCRQQEFK DRSGNCVLCK

51 QCGPGMELSK ECGFGYGEDA QCVPCRPHRF KEDWGFQKCK PCADCALVNR

101 FQRANCSHTS DAVCGDCLPG FYRKTKLVGF QDMECVPCGD PPPPYEPHCT

151 SKVNLVKISS TVSSPRDTAL AAVICSALAT VLLALLILCV IYCKRQFMEK

201 KPSCKLPSLC LTVK

SEQ ID NO: 3
MALKVLLEQEKTFFTLLVLLGYLSCKVTCESGDCRQQEFRDRSGNCVPCN

QCGPGMELSKECGFGYGEDAQCVTCRLHRFKEDWGFQKCKPCLDCAVVNR

FQKANCSATSDAICGDCLPGFYRKTKLVGFQDMECVPCGDPPPPYEPHCA

SKVNLVKIASTASSPRDTALAAVICSALATVLLALLILCVIYCKRQFMEK

KPSWSLRSQDIQYNGSELSCFDRPQLHEYAHRACCQCRRDSVQTCGPVRL

LPSMCCEEACSPNPATLGCGVHSAASLQARNAGPAGEMVPTFFGSLTQSI

CGEFSDAWPLMQNPMGGDNISFCDSYPELTGEDIHSLNPELESSTSLDSN

SSQDLVGGAVPVQSHSENFTAATDLSRYNNTLVESASTQDALTMRSQLDQ

ESGAVIHPATQTSLQEA

SEQ ID NO: 4
FYRKTKLVGFQDMECVPCGDPPPPYEPHCE*

SEQ ID NO: 5
  1 GGCACGAGGG CGTTTGGCGC GGAAGTGCTA CCAAGCTGCG GAAAGCGTCA

51 GTCTGGAGCA CAGCACTGGC GAGTAGCAGG AATAAACACG TTTGGTGAGA

101 GCCATGGCAC TCAAGGTCCT ACCTCTACAC AGGACGGTGC TCTTCGCTGC

151 CATTCTCTTC CTACTCCACC TGGCATGTAA AGTGAGTTGC GAAACCGGAG

201 ATTGCAGGCA GCAGGAATTC AAGGATCGAT CTGGAAACTG TGTCCTCTGC

251 AAACAGTGCG GACCTGGCAT GGAGTTGTCC AAGGAATGTG GCTTCGGCTA
```

```
301 TGGGGAGGAT GCACAGTGTG TGCCCTGCAG GCCGCACCGG TTCAAGGAAG

351 ACTGGGGTTT CCAGAAGTGT AAGCCATGTG CGGACTGTGC GCTGGTGAAC

401 CGCTTTCAGA GGGCCAACTG CTCACACACC AGTGATGCTG TCTGCGGGGA

451 CTGCCTGCCA GGATTTTACC GGAAGACCAA ACTGGTTGGT TTTCAAGACA

501 TGGAGTGTGT GCCCTGCGGA GACCCACCTC CTCCCTACGA ACCACACTGT

551 GAGTGATGTG CCAAGTGGCA GCAGACCTTT AAAAAAAAAA GAAAAAAAA
```

SEQ ID NO: 6
```
  1 CGGCACGAGG GCCGGCACCC CGCGCCACCC CAGCCTCAAA CTGCAGTCCG

51 GCGCCGCGGG GCAGGACAAG GGGAAGGAAT AAACACGTTT GGTGAGAGCC

101 ATGGCACTCA AGGTCCTACC TCTACACAGG ACGGTGCTCT TCGCTGCCAT

151 TCTCTTCCTA CTCCACCTGG CATGTAAAGT GAGTTGCGAA ACCGGAGATT

201 GCAGGCAGCA GGAATTCAAG GATCGATCTG AAACTGTGT CCTCTGCAAA

251 CAGTGCGGAC CTGGCATGGA GTTGTCCAAG GAATGTGGCT TCGGCTATGG

301 GGAGGATGCA CAGTGTGTGC CCTGCAGGCC GCACCGGTTC AAGGAAGACT

351 GGGGTTTCCA GAAGTGTAAG CCATGTGCGG ACTGTGCGCT GGTGAACCGC

401 TTTCAGAGGG CCAACTGCTC ACACACCAGT GATGCTGTCT GCGGGGACTG

451 CCTGCCAGGA TTTTACCGGA AGACCAAACT GGTTGGTTTT CAAGACATGG

501 AGTGTGTGCC CTGCGGAGAC CCACCTCCTC CCTACGAACC ACACTGTACC

551 AGCAAGGTGA ACCTTGTGAA GATCTCCTCC ACCGTCTCCA GCCCTCGGGA

601 CACGGCGCTG GCTGCCGTCA TCTGCAGTGC TCTGGCCACG GTGCTGCTCG

651 CCCTGCTCAT CCTGTGTGTC ATCTACTGCA AGAGGCAGTT CATGGAGAAG

701 AAACCCAGCT GTAAGCTCCC ATCCCTCTGT CTCACTGTGA AGTGAGCTTG

751 TTAGCATTGT CACCCAAGAG TTCTCAAGAC ACCTGGCTGA GACCTAAGAC

801 CTTTAGAGCA TCAACAGCTA CTTAGAATAC AAGATGCAGG AAAACGAGCC

851 TCTTCAGGAA TCTCAGGGCC TCCTAGGGAT GCTGGCAAGG CTGTGATGTC

901 TCAAGCTACC AGGAAAAATT TAAAGTTGTT TWTCCCCTAA AA
```

SEQ ID NO: 7
```
GAATTCCGGGGGAGGTGCACGGTGTGCACGCTGGACTGGACCCCCCATGC
AACCCCGCGCCCTGCGCCTTAACCAGGACTGCTCCGCGCGCCCCTGAGCC
TCGGGCTCCGGCCCGGACCTGCAGCCTCCCAGGTGCCTGGGAAGAACTCT
CCAACAATAAATACATTTGATAAGAAAGATGGCTTTAAAAGTGCTACTAG
AACAAGAGAAAACGTTTTTCACTCTTTTAGTATTACTAGGCTATTTGTCA
TGTAAAGTGACTTGTGAATCACGAGACTGTAGACAGCAAGAATTCAGGGA
TCGGTCTGGAAACTGTGTTCCCTGCAACCAGTGTGGGCCAGGCATGGAGT
TGTCTAAGGAATGTGGCTTCGGCTATGGGGAGGATGCACAGTGTGTGACG
TGCCGGCTGCACAGGTTCAAGGAGGACTGGGGCTTCCAGAAATGCAAGCC
CTGTCTGGACTGCGCAGTGGTGAACCGCTTTCAGAAGGCAAATTGTTCAG
CCACCAGTGATGCCATCTGCGGGGACTGCTTGCCAGGATTTTATAGGAAG
ACGAAACTTGTCGGCTTTCAAGACATGGAGTGTGTGCCTTGTGGAGACCC
TCCTCCTCCTTACGAACCGCACTGTGCCAGCAAGGTCAACCTCGTGAAGA
TCGCGTCCACGGCCTCCAGCCCACGGGACACGGCGCTGGCTGCCGTTATC
```

-continued
```
TGCAGCGCTCTGGCCACCGTCCTGCTGGCCCTGCTCATCCTCTGTGTCAT

CTATTGTAAGAGACAGTTTATGGAGAAGAAACCCAGCTGGTCTCTGCGGT

CGCAGGACATTCAGTACAACGGCTCTGAGCTGTCGTGTTTTGACAGACCT

CAGCTCCACGAATATGCCCACAGAGCCTGCTGCCAGTGCCGCCGTGACTC

AGTCCAGACCTGCGGGCCGGTGCGCTTGCTCCCATCCATGTGCTGTGAGG

AGGCCTGCAGCCCCAACCCGGCGACTCTTGGTTGTGGGGTGCATTCTGCA

GCCAGTCTTCAGGCAAGAAACGCAGGCCCAGCCGGGGAGATGGTGCCGAC

TTTCTTCGGATCCCTCACGCAGTCCATCTGTGGCGAGTTTTCAGATGCCT

GGCCTCTGATGCAGAATCCCATGGGTGGTGACAACATCTCTTTTTGTGAC

TCTTATCCTGAACTCACTGGAGAAGACATTCATTCTCTCAATCCAGAACT

TGAAAGCTCAACGTCTTTGGATTCAAATACCAGTCAAGATTTGGTTGGTG

GGGCTGTTCCAGTCCAGTCTCATTCTGAAAACTTTACAGCAGCTACTGAT

TTATCTAGATATAACAACACACTGGTAGAATCAGCATCAACTCAGGATGC

ACTAACTATGAGAAGCCAGCTAGATCAGGAGAGTGGCGCTGTCATCCACC

CAGCCACTCAGACGTCCCTCCAGGAAGCTTAAAGAACCTGCTTCTTTCTG

CAGTAGAAGCGTGTGCTGGAACCCAAAGAGTACTCCTTTGTTAGGCTTAT

GGACTGAGCAGTCTGGACCTTGCATGGCTTCTGGGGCAAAAATAAATCTG

AACGAAACTGACGGCATTTGAAGCCTTTCAGCCAGTTGCTTCTGAGCCAG

ACCAGCTGTAAGCTGAAACCTCAATGAATAACAAGAAAAGACTCCAGGCC

GACTCATGATACTCTGCATCTTTCCTACATGAGAAGCTTCTCTGCCACAA

AAGTGACTTCAAAGACGGATGGGTTGAGCTGGCAGCCTATGAGATTGTGG

ACATATAACAAGAAACAGAAATGCCCTCATGCTTATTTTCATGGTGATTG

TGGTTTTACAAGACTGAAGACCCAGAGTATACTTTTTCTTTCCAGAAATA

ATTTCATACCGCCTATGAAATATCAGATAAATTACCTTAGCTTTTATGTA

GAATGGGTTCAAAAGTGAGTGTTTCTATTTGAGAAGGACACTTTTTCATC

ATCTAAACTGATTCGCATAGGTGGTTAGAATGGCCCTCATATTGCCTGCC

TAAATCTTGGGTTTATTAGATGAAGTTTACTGAATCAGAGGAATCAGACA

GAGGAGGATAGCTCTTTCCAGAATCCACACTTCTGACCTCAGCCTCGGTC

TCATGAACACCCGCTGATCTCAGGAGAACACCTGGGCTAGGGAATGTGGT

CGAGAAAGGGCAGCCCATTGCCCAGAATTAACACA

SEQ ID NO: 8
GAATTCCAAATGCTAAAACCTAGTTCTTTATTCATCTATAAGGTATTTTG

TCGTTTAAGTTTCAATAAAAATGCCGAAGACCACTGACTTTATATTCCCC

CACCTGCACCCCCACCCCAATATAGAAGAAGTGCACTGAGAAGCATCTGC

AAAGTTAGCTTTAGGGGAATTGATATTTCTTAAGTGTCCACTGCTTCCTC

TTCAAAAATGTGTCTACCTAAGATACTATTATTTAAGCCTCTGTGTACTT

TTAACCGTAGAACTGGTAATGGAGACTGCTGGTAATTTATGACCACAACT

GTAAGCTTAGATGAAAGAGTTAACAAGGAGTATTTTCCTTTCTCTTCTAG

ATTTTATAGGAAGACGAAACTTGTCGGCTTTCAAGACATGGAGTGTGTGC

CTTGTGGAGACCCTCCTCCTCCTTACGAACGGCACTGTGAGTGAACGCAA

CACAGGCAGAGCCAAGGGGACGCCTGGCCTTTTGAAAAAGTTTAAATTTG
```

-continued

```
TAAACGTTTCTTCTCTGGCAGATGGACCCAAATCTGTCTCTCCTGTGGGG

TGTACAGTGTGTCCTCTTTAATCAGGCTTCTGGCAGGACAGAAAGTCCCT

TTGTTCTGTGCCTCAGTCAGCAAACCGGTCCCAGGGATTTGAATCTCAGA

GTGGAGTGCAGACATTTTGCCACTGCTCAGCTCCTTCTGAAGCCTTCCCT

GGCACCCTGGGTCTGTAATTCAGGCCACTTTGAATAACCAGGCGGCTCAC

ATCCTCACTCTTAGGTCTTCGTGCCCTGGCCCCATGAATTC

SEQ ID. NO. 9
MALKVLLEQEKTFFTLLVLLGYLSCKVTCESGDCRQQEFRDRSGNCVPCN

QCGPGMELSKECGFGYEDAQCVTCRLHRFKEDWGFQKCKPCLDCAVVNR

FQKANCSATSDAICGDCLPGFYRKTKLVGFQDMECVPCGDPPPPYEPHCE
```

---

We claim:

1. An isolated antibody that specifically binds to a human TNF Receptor in the BRAIN (TRAIN) polypeptide comprising an amino acid sequence selected from the group consisting of:
   (a) SEQ ID NO: 3;
   (b) SEQ ID NO: 9;
   (c) amino acid residues 26 to 417 of SEQ ID NO: 3;
   (d) amino acid residues 1 to 173 of SEQ ID NO: 3;
   (e) amino acid residues 26 to 173 of SEQ ID NO: 3;
   (f) amino acid residues 174 to 190 of SEQ ID NO: 3;
   (g) amino acid residues 191 to 417 of SEQ ID NO: 3.

2. The antibody of claim 1, wherein the antibody is a monoclonal antibody.

3. The monoclonal antibody of claim 2, wherein the antibody is a chimeric or humanized antibody comprising human constant regions.

4. The antibody of claim 1, wherein the antibody inhibits TRAIN receptor signaling.

5. The antibody of claim 1, wherein the antibody activates TRAIN receptor signaling.

6. A pharmaceutical composition comprising the antibody of claim 1 and a pharmaceutically acceptable carrier.

7. A pharmaceutical composition comprising the antibody of claim 2 and a pharmaceutically acceptable carrier.

8. A pharmaceutical composition comprising the antibody of claim 3 and a pharmaceutically acceptable carrier.

9. A pharmaceutical composition comprising the antibody of claim 4 and a pharmaceutically acceptable carrier.

10. A pharmaceutical composition comprising the antibody of claim 5 and a pharmaceutically acceptable carrier.

11. A method of treating a tumor in a patient wherein the tumor selectively expresses human TRAIN receptor, comprising the step of administering to the patient an amount of the antibody of claim 1 effective to treat the tumor.

* * * * *

SEQUENCE LISTING

<160> NUMBER OF SEQ ID NOS: 9

<210> SEQ ID NO 1
<211> LENGTH: 150
<212> TYPE: PRT
<213> ORGANISM: MUS MUSCULUS

<400> SEQUENCE: 1

```
Met Ala Leu Lys Val Leu Pro Leu His Arg Thr Val Leu Phe Ala Ala
  1               5                  10                  15

Ile Leu Phe Leu Leu His Leu Ala Cys Lys Val Ser Cys Glu Thr Gly
             20                  25                  30

Asp Cys Arg Gln Gln Glu Phe Lys Asp Arg Ser Gly Asn Cys Val Leu
         35                  40                  45

Cys Lys Gln Cys Gly Pro Gly Met Glu Leu Ser Lys Glu Cys Gly Phe
     50                  55                  60

Gly Tyr Gly Glu Asp Ala Gln Cys Val Pro Cys Arg Pro His Arg Phe
 65                  70                  75                  80

Lys Glu Asp Trp Gly Phe Gln Lys Cys Lys Pro Cys Ala Asp Cys Ala
                 85                  90                  95

Leu Val Asn Arg Phe Gln Arg Ala Asn Cys Ser His Thr Ser Asp Ala
            100                 105                 110

Val Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro Pro
    130                 135                 140

Tyr Glu Pro His Cys Glu
145                 150
```

<210> SEQ ID NO 2
<211> LENGTH: 214
<212> TYPE: PRT
<213> ORGANISM: Mus musculus

<400> SEQUENCE: 2

```
Met Ala Leu Lys Val Leu Pro Leu His Arg Thr Val Leu Phe Ala Ala
  1               5                  10                  15

Ile Leu Phe Leu Leu His Leu Ala Cys Lys Val Ser Cys Glu Thr Gly
             20                  25                  30
```

-continued

```
Asp Cys Arg Gln Gln Glu Phe Lys Asp Arg Ser Gly Asn Cys Val Leu
         35                  40                  45
Cys Lys Gln Cys Gly Pro Gly Met Glu Leu Ser Lys Glu Cys Gly Phe
 50                  55                  60
Gly Tyr Gly Glu Asp Ala Gln Cys Val Pro Cys Arg Pro His Arg Phe
 65                  70                  75                  80
Lys Glu Asp Trp Gly Phe Gln Lys Cys Lys Pro Cys Ala Asp Cys Ala
                 85                  90                  95
Leu Val Asn Arg Phe Gln Arg Ala Asn Cys Ser His Thr Ser Asp Ala
                100                 105                 110
Val Cys Gly Asp Cys Leu Pro Gly Phe Tyr Arg Lys Thr Lys Leu Val
        115                 120                 125
Gly Phe Gln Asp Met Glu Cys Val Pro Cys Gly Asp Pro Pro Pro Pro
    130                 135                 140
Tyr Glu Pro His Cys Thr Ser Lys Val Asn Leu Val Lys Ile Ser Ser
145                 150                 155                 160
Thr Val Ser Ser Pro Arg Asp Thr Ala Leu Ala Ala Val Ile Cys Ser
                165                 170                 175
Ala Leu Ala Thr Val Leu Leu Ala Leu Leu Ile Leu Cys Val Ile Tyr
                180                 185                 190
Cys Lys Arg Gln Phe Met Glu Lys Lys Pro Ser Cys Lys Leu Pro Ser
        195                 200                 205
Leu Cys Leu Thr Val Lys
    210

<210> SEQ ID NO 3
<211> LENGTH: 417
<212> TYPE: PRT
<213> ORGANISM: Homo sapiens

<400> SEQUENCE: 3

Met Ala Leu Lys Val Leu Leu Glu Gln Glu Lys Thr Phe Phe Thr Leu
 1               5                  10                  15
Leu Val Leu Leu Gly Tyr Leu Ser Cys Lys Val Thr Cys Glu Ser Gly
                20                  25                  30
Asp Cys Arg Gln Gln Glu Phe Arg Asp Arg Ser Gly Asn Cys Val Pro
         35                  40                  45
Cys Asn Gln Cys Gly Pro Gly Met Glu Leu Ser Lys Glu Cys Gly Phe
 50                  55                  60
Gly Tyr Gly Glu Asp Ala Gln Cys Val Thr Cys Arg Leu His Arg Phe
 65                  70                  75                  80
Lys Glu Asp Trp Gly Phe Gln Lys Cys Lys Pro Cys Leu Asp Cys Ala
                 85                  90                  95
Val Val Asn Arg Phe Gln Lys Ala Asn Cys Ser Ala Thr Ser Asp Ala
                100                 105                 110
Ile Cys Gly Asp Cys Leu Pro Gly Phe Tyr Arg Lys Thr Lys Leu Val
        115                 120                 125
Gly Phe Gln Asp Met Glu Cys Val Pro Cys Gly Asp Pro Pro Pro Pro
    130                 135                 140
Tyr Glu Pro His Cys Ala Ser Lys Val Asn Leu Val Lys Ile Ala Ser
145                 150                 155                 160
Thr Ala Ser Ser Pro Arg Asp Thr Ala Leu Ala Ala Val Ile Cys Ser
                165                 170                 175
Ala Leu Ala Thr Val Leu Leu Ala Leu Leu Ile Leu Cys Val Ile Tyr
                180                 185                 190
```

-continued

Cys Lys Arg Gln Phe Met Glu Lys Pro Ser Trp Ser Leu Arg Ser
         195                 200                 205

Gln Asp Ile Gln Tyr Asn Gly Ser Glu Leu Ser Cys Phe Asp Arg Pro
    210                 215                 220

Gln Leu His Glu Tyr Ala His Arg Ala Cys Gln Cys Arg Arg Asp
225                 230                 235                 240

Ser Val Gln Thr Cys Gly Pro Val Arg Leu Pro Ser Met Cys Cys
             245                 250                 255

Glu Glu Ala Cys Ser Pro Asn Pro Ala Thr Leu Gly Cys Gly Val His
             260                 265                 270

Ser Ala Ala Ser Leu Gln Ala Arg Asn Ala Gly Pro Ala Gly Glu Met
    275                 280                 285

Val Pro Thr Phe Phe Gly Ser Leu Thr Gln Ser Ile Cys Gly Glu Phe
    290                 295                 300

Ser Asp Ala Trp Pro Leu Met Gln Asn Pro Met Gly Gly Asp Asn Ile
305                 310                 315                 320

Ser Phe Cys Asp Ser Tyr Pro Glu Leu Thr Gly Glu Asp Ile His Ser
             325                 330                 335

Leu Asn Pro Glu Leu Glu Ser Ser Thr Ser Leu Asp Ser Asn Ser Ser
             340                 345                 350

Gln Asp Leu Val Gly Gly Ala Val Pro Val Gln Ser His Ser Glu Asn
    355                 360                 365

Phe Thr Ala Ala Thr Asp Leu Ser Arg Tyr Asn Asn Thr Leu Val Glu
    370                 375                 380

Ser Ala Ser Thr Gln Asp Ala Leu Thr Met Arg Ser Gln Leu Asp Gln
385                 390                 395                 400

Glu Ser Gly Ala Val Ile His Pro Ala Thr Gln Thr Ser Leu Gln Glu
                405                 410                 415

Ala

<210> SEQ ID NO 4
<211> LENGTH: 30
<212> TYPE: PRT
<213> ORGANISM: Homo sapiens

<400> SEQUENCE: 4

Phe Tyr Arg Lys Thr Lys Leu Val Gly Phe Gln Asp Met Glu Cys Val
1               5                   10                  15

Pro Cys Gly Asp Pro Pro Pro Tyr Glu Pro His Cys Glu
            20                  25                  30

<210> SEQ ID NO 5
<211> LENGTH: 599
<212> TYPE: DNA
<213> ORGANISM: Mus musculus

<400> SEQUENCE: 5
ggcacgaggg cgtttggcgc ggaagtgcta ccaagctgcg gaaagcgtga gtctggagca      60
cagcactggc gagtagcagg aataaacacg tttggtgaga gccatggcac tcaaggtcct     120
acctctacac aggacggtgc tcttcgctgc cattctcttc ctactccacc tggcatgtaa     180
agtgagttgc gaaaccggag attgcaggca gcaggaattc aaggatcgat ctggaaactg     240
tgtcctctgc aaacagtgcg gacctggcat ggagttgtcc aaggaatgtg gcttcggcta     300
tggggaggat gcacagtgtg tgccctgcag gccgcaccgg ttcaaggaag actggggttt     360

```
ccagaagtgt aagccatgtg cggactgtgc gctggtgaac cgctttcaga gggccaactg    420
ctcacacacc agtgatgctg tctgcgggga ctgcctgcca ggattttacc ggaagaccaa    480
actggttggt tttcaagaca tggagtgtgt gccctgcgga gacccacctc ctccctacga    540
accacactgt gagtgatgtg ccaagtggca gcagaccttt aaaaaaaaaa gaaaaaaaa    599

<210> SEQ ID NO 6
<211> LENGTH: 942
<212> TYPE: DNA
<213> ORGANISM: Mus musculus

<400> SEQUENCE: 6
cggcacgagg gccggcaccc cgcgccaccc cagcctcaaa ctgcagtccg gcgccgcggg     60
gcaggacaag gggaaggaat aaacacgttt ggtgagagcc atggcactca aggtcctacc    120
tctacacagg acggtgctct tcgctgccat tctcttccta ctccacctgg catgtaaagt    180
gagttgcgaa accggagatt gcaggcagca ggaattcaag gatcgatctg aaactgtgt    240 cctctgcaaa cagtgcggac ctggcatgga gttgtccaag aatgtggct tcggctatgg    300 ggaggatgca cagtgtgtgc cctgcaggcc gcaccggttc aaggaagact ggggtttcca    360
gaagtgtaag ccatgtgcgg actgtgcgct ggtgaaccgc tttcagaggg ccaactgctc    420
acacaccagt gatgctgtct gcggggactg cctgccagga ttttaccgga agaccaaact    480
ggttggtttt caagacatgg agtgtgtgcc ctgcggagac ccacctcctc cctacgaacc    540
acactgtacc agcaaggtga accttgtgaa gatctcctcc accgtctcca gcctcgggga    600
cacggcgctg gctgccgtca tctgcagtgc tctggccacg gtgctgctcg ccctgctcat    660
cctgtgtgtc atctactgca agaggcagtt catggagaag aaacccagct gtaagctccc    720
atccctctgt ctcactgtga agtgagcttg ttagcattgt cacccaagag ttctcaagac    780
acctggctga gacctaagac ctttagagca tcaacagcta cttagaatac aagatgcagg    840
aaaacgagcc tcttcaggaa tctcagggcc tcctagggat gctggcaagg ctgtgatgtc    900
tcaagctacc aggaaaaatt taagttgtt twtcccctaa aa                      942

<210> SEQ ID NO 7
<211> LENGTH: 2185
<212> TYPE: DNA
<213> ORGANISM: Homo sapiens

<400> SEQUENCE: 7
gaattccggg ggaggtgcac ggtgtgcacg ctggactgga cccccatgc aaccccgcgc     60 cctgcgcctt aaccaggact gctccgcgcg cccctgagcc tcgggctccg gcccggacct    120
gcagcctccc agtggctggg aagaactct ccaacaataa atacatttga taagaaagat    180 gctttaaaa gtgctactag aacaagagaa aacgttttc actctttag tattactagg    240 ctatttgtca tgtaaagtga cttgtgaatc aggagactgt agacagcaag aattcaggga    300
tcggtctgga aactgtgttc cctgcaacca gtgtgggcca ggcatggagt tgtctaagga    360
atgtggcttc ggctatgggg aggatgcaca gtgtgtgacg tgccggctgc acaggttcaa    420
ggaggactgg ggcttccaga atgcaagcc ctgtctggac tgcgcagtgg tgaaccgctt    480
tcagaaggca aattgttcag ccaccagtga tgccatctgc ggggactgct tgccaggatt    540
ttataggaag acgaaacttg tcggctttca agacatggag tgtgtgcctt gtggagaccc    600
tcctcctcct tacgaaccgc actgtgccag caaggtcaac ctcgtgaaga tcgcgtccac    660
ggcctccagc ccacgggaca cggcgctggc tgccgttatc tgcagcgctc tggccaccgt    720
```

```
cctgctggcc ctgctcatcc tctgtgtcat ctattgtaag agacagttta tggagaagaa      780
acccagctgg tctctgcggt cgcaggacat tcagtacaac ggctctgagc tgtcgtgttt      840
tgacagacct cagctccacg aatatgccca cagagcctgc tgccagtgcc gccgtgactc      900
agtgcagacc tgcgggccgg tgcgcttgct cccatccatg tgctgtgagg aggcctgcag      960
ccccaacccg cgcactcttg gttgtggggt gcattctgca gccagtcttc aggcaagaaa     1020
cgcaggccca gccggggaga tggtgccgac tttcttcgga tccctcacgc agtccatctg     1080
tggcgagttt tcagatgcct ggcctctgat gcagaatccc atgggtggtg acaacatctc     1140
tttttgtgac tcttatcctg aactcactgg agaagacatt cattctctca atccagaact     1200
tgaaagctca acgtctttgg attcaaatag cagtcaagat ttggttggtg gggctgttcc     1260
agtccagtct cattctgaaa actttacagc agctactgat ttatctagat ataacaacac     1320
actggtagaa tcagcatcaa ctcaggatgc actaactatg agaagccagc tagatcagga     1380
gagtggcgct gtcatccacc cagccactca gacgtccctc caggaagctt aaagaacctg     1440
cttctttctg cagtagaagc gtgtgctgga acccaaagag tactcctttg ttaggcttat     1500
ggactgagca gtctggacct tgcatggctt ctggggcaaa aataaatctg aaccaaactg     1560
acggcatttg aagcctttca gccagttgct tctgagccag accagctgta agctgaaacc     1620
tcaatgaata acaagaaaag actccaggcc gactcatgat actctgcatc tttcctacat     1680
gagaagcttc tctgccacaa aagtgacttc aaagacggat gggttgagct ggcagcctat     1740
gagattgtgg acatataaca agaaacagaa atgccctcat gcttattttc atggtgattg     1800
tggttttaca agactgaaga cccagagtat acttttcctt ccagaaaata atttcatacc     1860
gcctatgaaa tatcagataa attaccttag cttttatgta gaatgggttc aaaagtgagt     1920
gtttctattt gagaaggaca cttttcatc atctaaactg attcgcatag gtggttagaa      1980
tggccctcat attgcctgcc taaatcttgg gtttattaga tgaagtttac tgaatcagag     2040
gaatcagaca gaggaggata gctctttcca gaatccacac ttctgacctc agcctcggtc     2100
tcatgaacac ccgctgatct caggagaaca cctgggctag gaatgtggt cgagaaaggg      2160
cagcccattg cccagaatta acaca                                            2185

<210> SEQ ID NO 8
<211> LENGTH: 791
<212> TYPE: DNA
<213> ORGANISM: Homo sapiens

<400> SEQUENCE: 8
gaattccaaa tgctaaaacc tagttcttta ttcatctata aggtattttg tcgtttaagt       60
ttcaataaaa atgccgaaga ccactgactt tatattcccc cacctgcacc cccaccccaa      120
tatagaagaa gtgcactgag aagcatctgc aaagttagct ttaggggaat tgatatttct      180
taagtgtcca ctgcttcctc ttcaaaaatg tgtctaccta agatactatt atttaagcct      240
ctgtgtactt ttaaccgtag aactggtaat ggagactgct ggtaatttat gaccacaact      300
gtaagcttag atgaaagagt taacaaggag tattttcctt tctcttctag attttatagg      360
aagacgaaac ttgtcggctt tcaagacatg gagtgtgtgc cttgtggaga ccctcctcct      420
ccttacgaac cgcactgtga gtgaacgcaa cacaggcaga gccaagggga cgcctggcct      480
tttgaaaaag tttaaatttg taaacgtttc ttctctggca gatggagcca aatctgtctc      540
tcctgtgggg tgtacagtgt gtcctctttta atcaggcttg tggcaggaca gaaagtccct      600
```

-continued

```
ttgttctgtg cctcagtcag caaaccggtc ccagggattt gaatctcaga gtggagtgca      660
gacattttgc cactgctcag ctccttctga agccttccct ggcaccctgg gtctgtaatt      720
caggccactt tgaataacca ggcggctcac atcctcactc ttaggtcttc gtgccctggc      780
cccatgaatt c                                                           791
```

<210> SEQ ID NO 9
<211> LENGTH: 150
<212> TYPE: PRT
<213> ORGANISM: Homo sapiens

<400> SEQUENCE: 9

```
Met Ala Leu Lys Val Leu Leu Glu Gln Glu Lys Thr Phe Phe Thr Leu
  1               5                  10                  15

Leu Val Leu Leu Gly Tyr Leu Ser Cys Lys Val Thr Cys Glu Ser Gly
                 20                  25                  30

Asp Cys Arg Gln Gln Glu Phe Arg Asp Arg Ser Gly Asn Cys Val Pro
             35                  40                  45

Cys Asn Gln Cys Gly Pro Gly Met Glu Leu Ser Lys Glu Cys Gly Phe
         50                  55                  60

Gly Tyr Gly Glu Asp Ala Gln Cys Val Thr Cys Arg Leu His Arg Phe
 65                  70                  75                  80

Lys Glu Asp Trp Gly Phe Gln Lys Cys Lys Pro Cys Leu Asp Cys Ala
                 85                  90                  95

Val Val Asn Arg Phe Gln Lys Ala Asn Cys Ser Ala Thr Ser Asp Ala
                100                 105                 110

Ile Cys Gly Asp Cys Leu Pro Gly Phe Tyr Arg Lys Thr Lys Leu Val
                115                 120                 125

Gly Phe Gln Asp Met Glu Cys Val Pro Cys Gly Asp Pro Pro Pro Pro
            130                 135                 140

Tyr Glu Pro His Cys Glu
145                 150
```